(12) United States Patent
Chou et al.

(10) Patent No.: US 7,468,031 B2
(45) Date of Patent: Dec. 23, 2008

(54) MEDICAL MEASURING APPARATUS

(75) Inventors: Yu-Wang Chou, Rende Township, Tainan County (TW); Su-Chen Cheng, Chung Ho (TW)

(73) Assignee: Health & Life Co., Ltd., Taipei (TW)

( * ) Notice: Subject to any disclaimer, the term of this patent is extended or adjusted under 35 U.S.C. 154(b) by 0 days.

(21) Appl. No.: 11/652,573

(22) Filed: Jan. 12, 2007

(65) Prior Publication Data

US 2008/0171917 A1    Jul. 17, 2008

(51) Int. Cl.
*A61B 5/00* (2006.01)
(52) U.S. Cl. ............... 600/300; 600/301; 128/903; 128/904; 128/905; 128/920
(58) Field of Classification Search .......... 600/300, 600/301; 128/903–905, 920
See application file for complete search history.

(56) References Cited

U.S. PATENT DOCUMENTS

| 5,640,953 A * | 6/1997 | Bishop et al. ............... 600/300 |
| 6,761,459 B1 * | 7/2004 | Arsenich .................... 353/122 |

* cited by examiner

*Primary Examiner*—Michael C Astorino
*Assistant Examiner*—Kai Rajan
(74) *Attorney, Agent, or Firm*—Rosenberg, Klein & Lee

(57) ABSTRACT

This invention discloses a medical measuring apparatus that includes a medical measuring body and a transparent display unit. The medical measuring body is used for measuring at least one physiological information such as body temperature, pulse, blood pressure, blood sugar, blood oxygen, uric acid, cholesterol, pH value, body fat or bone density. The transparent display unit includes two corresponding display surfaces for displaying the physiological information, and the two display surface are mirrored or inverted, so that the two display surfaces can display identical physiological information to provide different view angles from different directions.

8 Claims, 7 Drawing Sheets

MEDICAL MEASURING APPARATUS

BACKGROUND OF THE INVENTION

1. Field of the Invention

The present invention relates to a medical measuring apparatus, and more particularly to a medical measuring apparatus adopting a transparent display unit having two corresponding display surfaces.

2. Description of the Related Art

Referring to FIG. 1 for a schematic view of an example of a conventional medical measuring apparatus, the medical measuring apparatus 1 is a blood pressure meter, and such medical measuring apparatus 1 comprises a medical measuring body 10, a display screen 11, a duct 12 and a cuff 13. The medical measuring body 10 is used for measuring the physiological information of blood pressure through the duct 12 and cuff 13, and then the measured result is displayed in a form of image, figure or word on the display screen 11.

Referring to FIG. 2 for a schematic view of another example of a Conventional medical measuring apparatus, the medical measuring apparatus 2 is a multifunctional physiological meter, and this medical measuring apparatus 2 comprises a medical measuring body 20 and a display screen 21, wherein the medical measuring body 20 comprises a CPU 201, an I/O circuit 202, a user input unit 203, a memory unit 204, a body fat measuring unit 205, a blood pressure measuring unit 206, a blood sugar measuring unit 207, a body temperature measuring unit 208 and a low frequency output unit 209. The CPU 201 is electrically connected the measuring units 205, 206, 207, 208, and 209 through the I/O circuit 202 for electric conversions, and then the CPU 201 operates with the memory unit 204 and finally the display screen 21 displays the measured information of the measuring units 205, 206, 207, 208, and 209 through a control signal of the user input unit 203.

Referring to FIG. 3 for a schematic view of an operation of a medical measuring apparatus as depicted in FIG. 2, a user inserts a blood sugar test strip 30 into the medical measuring apparatus 2, and sets and starts the blood sugar measuring unit 207 from the user input unit 203 to perform a measurement of blood sugar by the blood sugar test strip 30, and the blood sugar measuring unit 207 sends the related measured electric signals through the I/O circuit 202 to the CPU 201 and operates with the memory unit 204, and finally the display screen 21 displays the measured data or result of the blood sugar test strip 30.

In addition, the conventional medical measuring apparatus generally indicates the measured physiological information in the form of image, figure, word or voice through a display device for providing users a convenient way of viewing the displayed data, caption or result on the display screen. However, such design ignores the situations of having several viewers such as a nurse, a doctor and a patient, or a medical professional and a patient, or a nurse, a doctor, a patient and a patient's relatives, or a medical professional, a patient and a patient's relatives at a time. Almost all viewers stand in front of the display screen, and thus making the medical measuring practice very inconvenient. To solve this problem, many medical service units add more screens for the viewers from different directions. Such arrangement not only increases costs, but also causes inconvenience for the use of the medical measuring apparatus since additional cables are connected to the screens.

In view of shortcomings of the prior art, the inventor of the present invention based on years of experience in the medical measuring apparatus related industry to conduct extensive researches and experiments, and finally developed a medical measuring apparatus in accordance with the present invention to overcome the aforementioned shortcomings.

SUMMARY OF THE INVENTION

In view of the shortcomings of the prior art, the present invention provides a medical measuring apparatus that comes with a single display screen having different viewing angles to avoid the inconvenience of requiring viewers to stand at a position in front of the display screen for their views.

Another objective of the present invention is to provide a medical measuring apparatus that comes with a single display screen having different viewing angles to avoid installing several different screens to meet the requirements for the view by several viewers at different directions and positions, and also save the hardware cost for installing additional screens and connecting additional transmission lines.

A further objective of the present invention is to provide a medical measuring apparatus that can overcome the shortcomings of the prior art and maintain good portability and convenience of the medical measuring apparatus.

To achieve the foregoing objectives, the present invention provides a medical measuring apparatus that comprises a medical measuring body and a transparent display unit, wherein the medical measuring body is used for measuring at least one physiological information such as body temperature, pulse, blood pressure, blood sugar, blood oxygen, uric acid, cholesterol, pH value, body fat or bone density, and the transparent display unit includes two corresponding display surfaces, and the transparent display unit is used for displaying the aforementioned physiological information in a form of image, figure or word. In addition, the display surface of the transparent display unit are mirrored or inverted, so that the display surfaces can display identical physiological information. To provide better viewing quality for viewers, the transparent display unit further includes a light source for assisting the illumination and the display. The light source of the transparent display unit may further include at least one color light, such that the transparent display unit can have a color change for the display. It is noteworthy to point out that the transparency of the transparent display unit can fall within the range from 0% to 100% according to the required design, or the transparent display unit can be a transparent display unit having a lens with at least one color.

To make it easier for our examiner to understand the technical characteristics and effects of the present invention, we use preferred embodiments together with the attached drawings for the detailed description of the present invention.

DETAILED DESCRIPTION OF THE PREFERRED EMBODIMENTS

Figure 1:
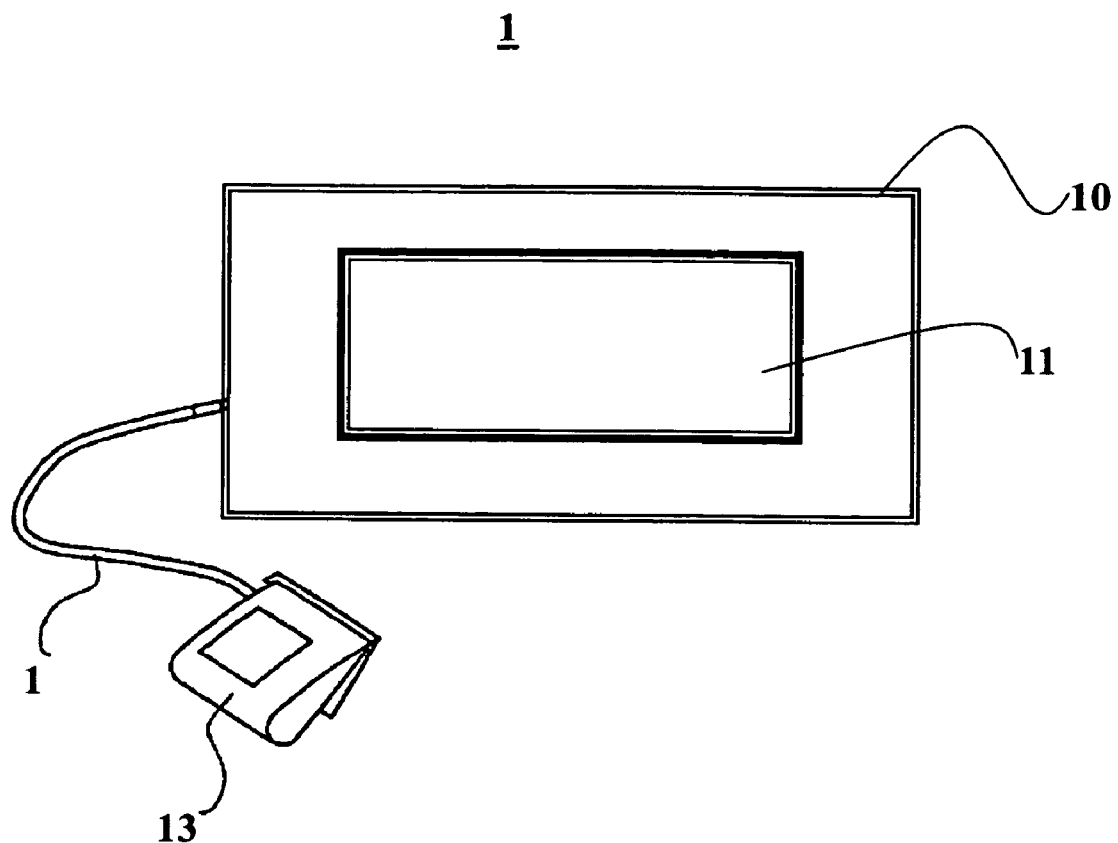
FIG. 1 is a schematic view of an example of a conventional medical measuring apparatus.
Figure 2:
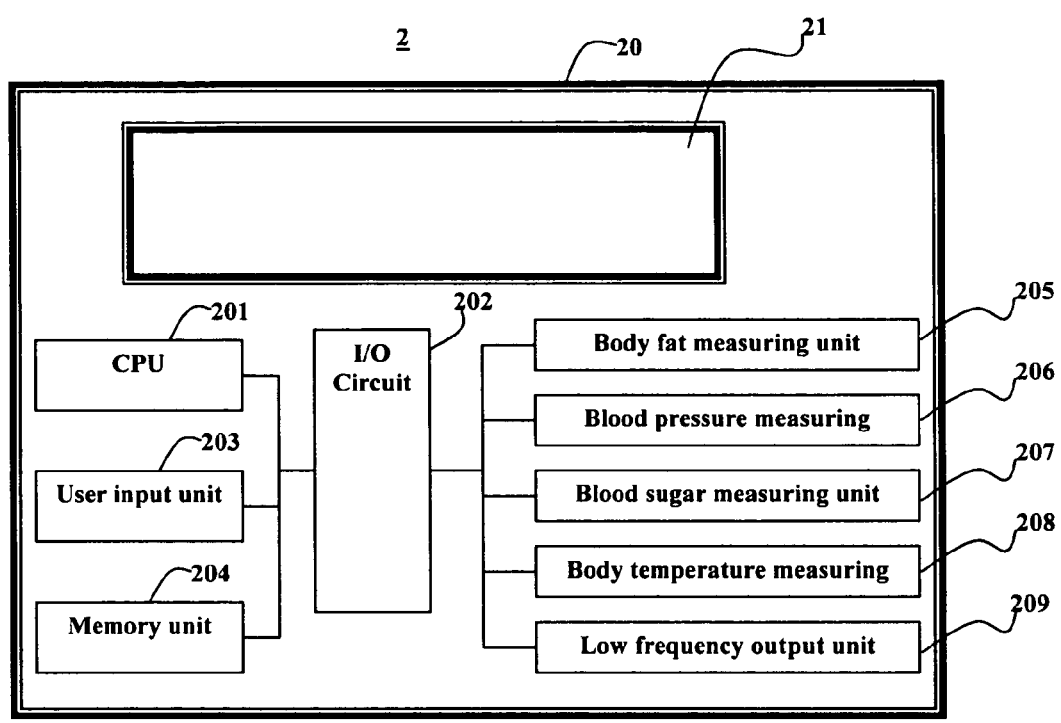
FIG. 2 is a schematic view of another example of a conventional medical measuring apparatus.
Figure 3:
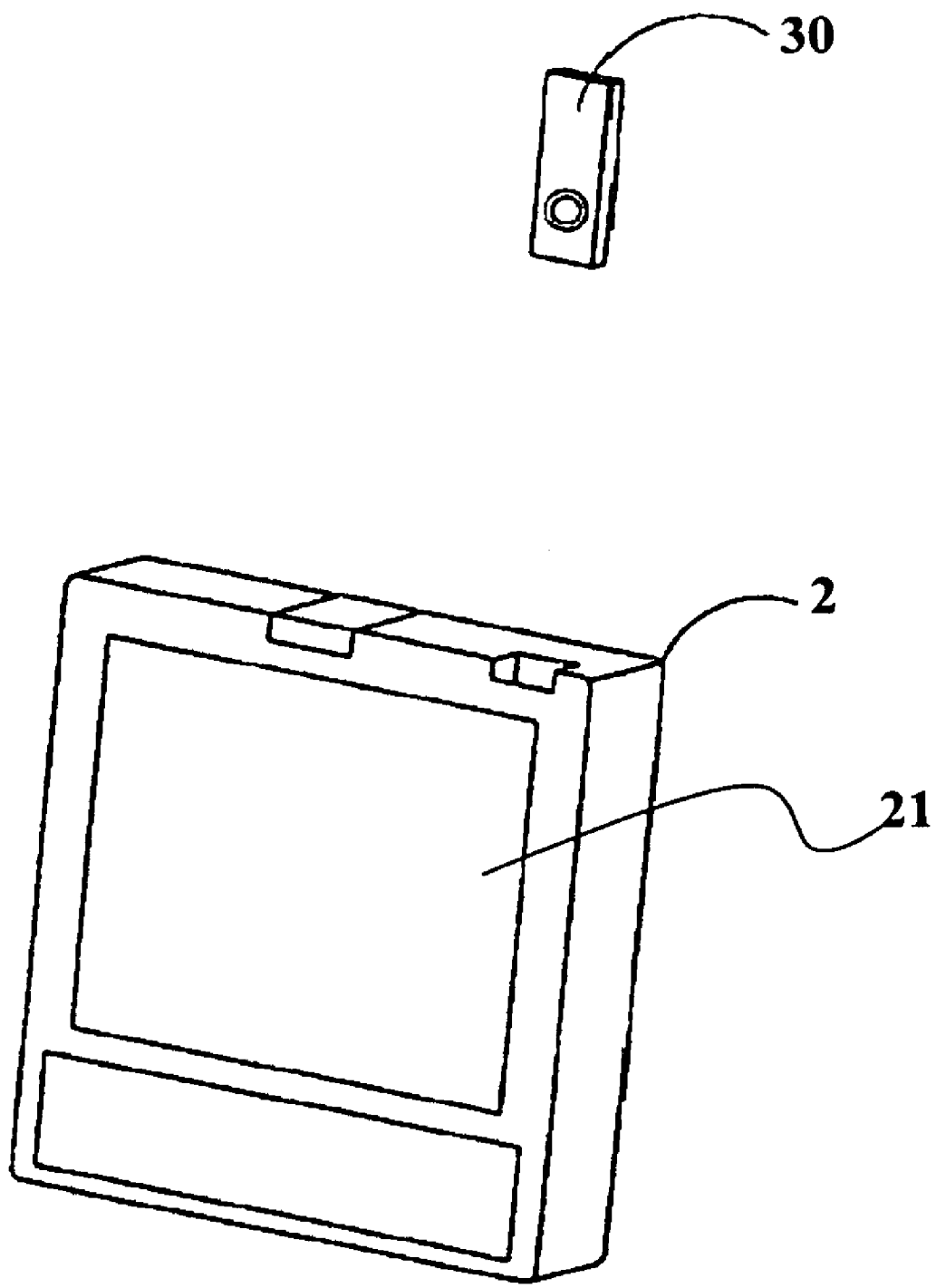
FIG. 3 is a schematic view of the operation of an example of a conventional medical measuring apparatus.

In describing a preferred embodiment of medical measuring apparatus in accordance with the invention illustrated in the drawings, specific terminologies and numerals will be resorted to for the sake of clarity. However, the invention is not intended to be limited to the specific terms and numerals so selected, and it is to be understood that each specific term includes all technical equivalents which operate in a similar manner to accomplish a similar purpose.

Figure 4:
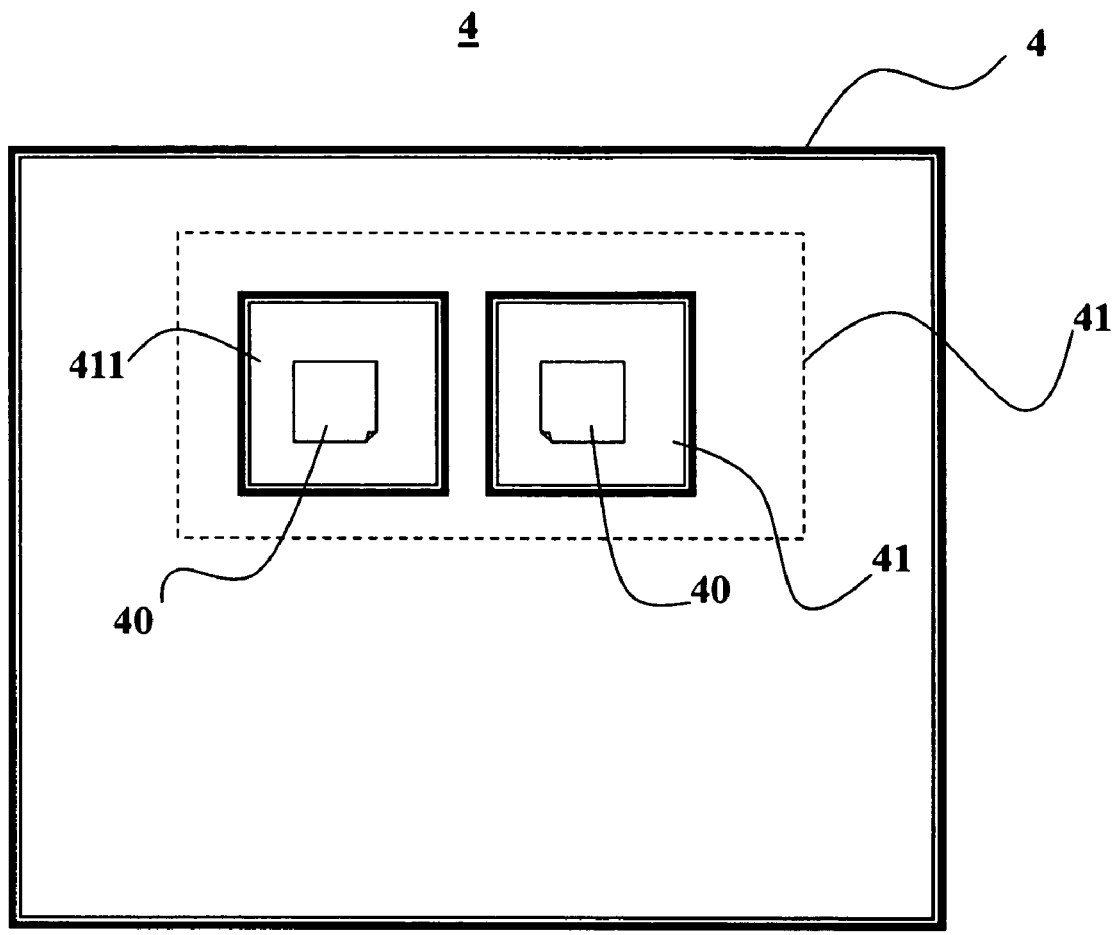
FIG. 4 is a schematic block diagram of a medical measuring apparatus of the present invention.

Referring to FIG. 4 for a schematic block diagram of a medical measuring apparatus of the present invention, the medical measuring apparatus 4 comprises a medical measuring body 40 and a transparent display unit 41. In this embodiment, the medical measuring body 40 is used for measuring a user's physiological information 401. The transparent display unit 41 includes a first display surface 411 and a second display surface 412 for displaying the user's physiological information 401 at the same time.

Figure 5:
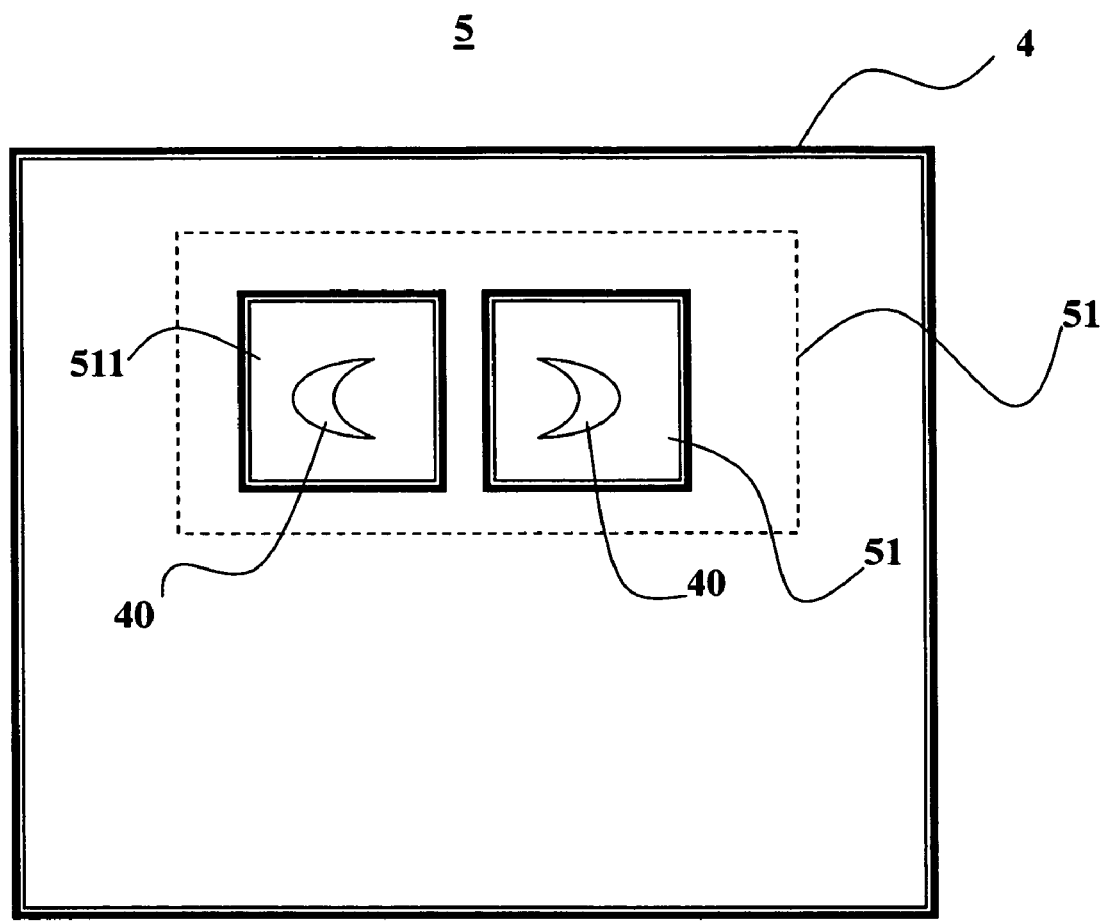
FIG. 5 is another schematic block diagram of a medical measuring apparatus of the present invention.

Referring to FIG. 5 for another schematic block diagram of a medical measuring apparatus of the present invention, the medical measuring apparatus 5 comprises a medical measuring body 40 and a transparent display lens 51. In this embodiment, the medical measuring body 40 is used for measuring a user's physiological information 401. The transparent display lens 51 is used for displaying the user's physiological information 401 at a front-side display surface 511, while a back-side display surface 512 of the transparent display lens 51 allows users to view identical physiological information 401. However, the image viewed from back-side display surface 512 is inverted sideways. Therefore, the image at the back-side display surface 512 can be mirrored or inverted to produce identical images of the physiological information 401 for the back-side display surface 512 and the front-side display surface 511.

Figure 6:
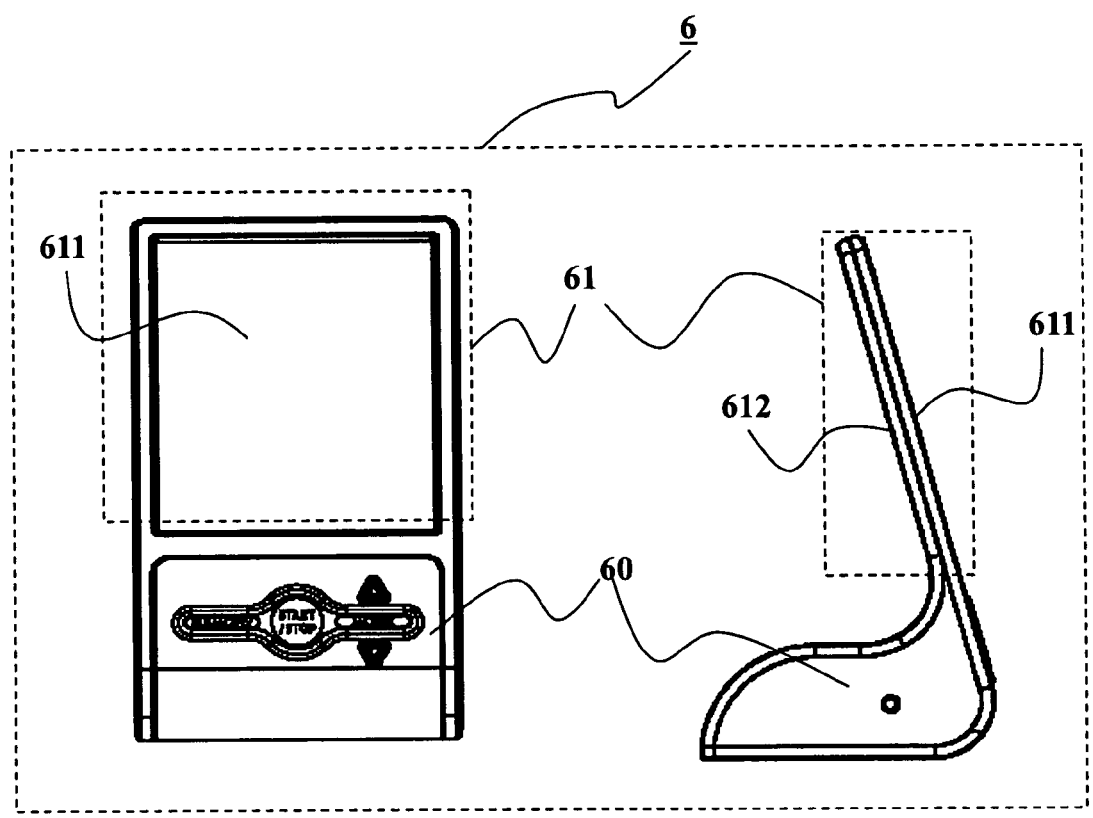
FIG. 6 is a schematic view of a medical measuring apparatus in accordance with another preferred embodiment of the present invention.

Referring to FIG. 6 for a schematic view of a medical measuring apparatus in accordance with another preferred embodiment of the present invention, the medical measuring apparatus 6 comprises a medical measuring body 60 and a transparent display screen 61. In the figure, the transparent display screen 61 includes a first display surface 611 and a second display surface 612 that provide different viewing angles for viewers on both sides to read the user's physiological information measured by the medical measuring body 60.

Figure 7:
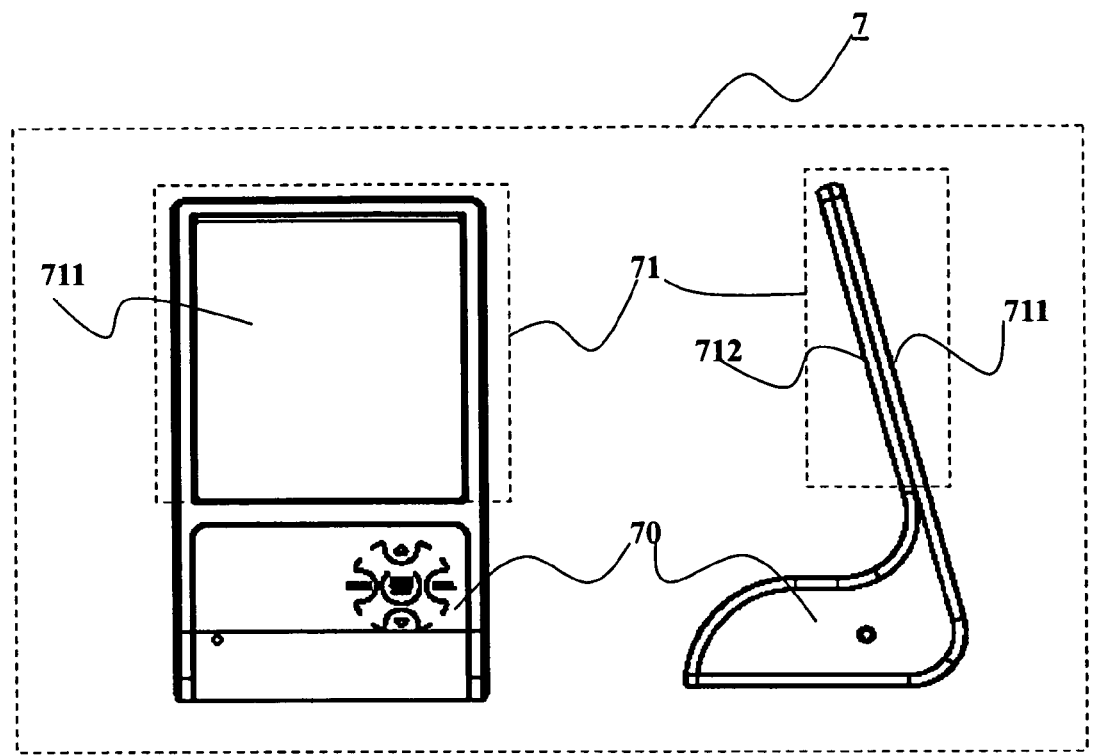
FIG. 7 is a schematic view of a medical measuring apparatus with a different stylish appearance in according with another preferred embodiment of the present invention.

Referring to FIG. 7 for a schematic view of a medical measuring apparatus with a different stylish appearance in according with another preferred embodiment of the present invention, the medical measuring apparatus 7 comprises a medical measuring body 70 and a transparent display screen 71. In the figure, the transparent display screen 71 similar to the one illustrated in FIG. 6 also includes a first display surface 711 and a second display surface 712 that that provide different viewing angles for viewers on both sides to read the user's physiological information measured by the medical measuring body 70.

While the invention has been described by means of specific embodiments, numerous modifications and variations could be made thereto by those skilled in the art without departing from the scope and spirit of the invention set forth in the claims.

What is claimed is:

1. A medical measuring apparatus, comprising:
    a medical measuring body for measuring at least one physiological metric and obtaining physiological information; and
    a transparent display unit having a first and second opposing display surfaces, said transparent display unit for displaying a positive image and an inverted image, said positive image being viewed on said first display surface and said inverted image being viewed on said second display surface thereby providing said positive image to be viewed from said second display surface through said transparent unit for displaying physiological information.

2. The medical measuring apparatus of claim 1, wherein said physiological information is shown in a form of image, figure or word.

3. The medical measuring apparatus of claim 1, wherein said display surfaces of said transparent display unit are mirrored or inverted to display identical physiological information on said display surfaces.

4. The medical measuring apparatus of claim 1, wherein said transparent display unit has at least one light source for assisting the illumination and display.

5. The medical measuring apparatus of claim 1, wherein said transparent display unit includes the light source with at least one color light for the illumination and display, so that said transparent display unit produces a color change.

6. The medical measuring apparatus of claim 1, wherein said transparent display unit has a transparency ranging from 0% to 100%.

7. The medical measuring apparatus of claim 1, wherein said transparent display unit includes a lens with at least one color.

8. The medical measuring apparatus of claim 1, wherein said physiological information includes body temperature, pulse, blood pressure, blood sugar, blood oxygen, uric acid, cholesterol, pH value, body fat or bone density.

* * * * *